US012567612B1

(12) United States Patent
Zhang et al.

(10) Patent No.: US 12,567,612 B1
(45) Date of Patent: Mar. 3, 2026

(54) MONITORING AND EARLY WARNING SYSTEM FOR POWER LITHIUM ION BATTERY TRANSPORT CASE AND MONITORING AND EARLY WARNING METHOD

(71) Applicant: CHONGQING JIAOTONG UNIVERSITY, Chongqing (CN)

(72) Inventors: Ping Zhang, Chongqing (CN);
Kaixuan Wang, Chongqing (CN);
Jinzhong Wu, Chongqing (CN);
Wenjun Liu, Chongqing (CN); Yujie Cui, Chongqing (CN); Yuxing Gou, Chongqing (CN); Huan Bao, Chongqing (CN)

(73) Assignee: CHONGQING JIAOTONG UNIVERSITY, Chongqing (CN)

( * ) Notice: Subject to any disclaimer, the term of this patent is extended or adjusted under 35 U.S.C. 154(b) by 0 days.

(21) Appl. No.: 19/321,760

(22) Filed: Sep. 8, 2025

(30) Foreign Application Priority Data

Apr. 11, 2025 (CN) .......................... 202510453796.4

(51) Int. Cl.
*A62C 3/16* (2006.01)
*A62C 2/24* (2006.01)
(Continued)

(52) U.S. Cl.
CPC ........... *H01M 10/488* (2013.01); *A62C 2/247* (2013.01); *A62C 3/16* (2013.01); *G01K 1/024* (2013.01);
(Continued)

(58) Field of Classification Search
CPC .......... A62C 2/247; A62C 3/16; G01K 1/024; G01N 33/005; G08B 5/38; G08B 17/10;
(Continued)

(56) References Cited

U.S. PATENT DOCUMENTS 4,839,527 A * 6/1989 Leitch .................. G08B 17/103
340/630

FOREIGN PATENT DOCUMENTS

CN 112950886 A * 6/2021 ............. A62C 31/12
CN 117018504 A * 11/2023 ............... A62C 3/16

OTHER PUBLICATIONS

CN 112950886 A—Machine translation, retrieved on Nov. 2025 (Year: 2025).*

(Continued)

*Primary Examiner* — James M Erwin
*Assistant Examiner* — Gilberto Ramos Rivera
(74) *Attorney, Agent, or Firm* — HOWARD M COHN and Associates, LLC

(57) ABSTRACT

The present invention discloses a thermal runaway monitoring and early warning system and method for a power lithium ion battery in a transport case. The system includes a monitoring unit, a data processing unit, a data transmission unit, a power supply unit, a display unit, and the like. The monitoring unit contains infrared array temperature sensors, gas sensors, smoke sensors, and pressure sensors, which are arranged using a distributed scheme to monitor the inside of the transport case. The data transmission unit sends early warning information to a terminal. According to a multi-information monitoring-based thermal runaway early warning method under different transport conditions, different transport condition data and data of the battery in the transport case are fused. A clustering algorithm and an ensemble learning algorithm are involved, and a lithium ion battery thermal runaway risk level is quantified, thereby improving the early warning accuracy.

8 Claims, 3 Drawing Sheets

(51) Int. Cl.

| | |
|---|---|
| *G01K 1/024* | (2021.01) |
| *G01N 33/00* | (2006.01) |
| *G08B 5/38* | (2006.01) |
| *G08B 17/10* | (2006.01) |
| *G08B 21/18* | (2006.01) |
| *G08B 25/10* | (2006.01) |
| *H01M 10/48* | (2006.01) |

(52) U.S. Cl.
CPC ............. *G01N 33/005* (2013.01); *G08B 5/38* (2013.01); *G08B 17/10* (2013.01); *G08B 21/182* (2013.01); *G08B 21/185* (2013.01); *G08B 25/10* (2013.01); *H01M 10/486* (2013.01)

(58) Field of Classification Search
CPC .... G08B 21/182; G08B 21/185; G08B 25/10; H01M 10/486; H01M 10/488
USPC ......................................................... 429/90
See application file for complete search history.

(56) References Cited

OTHER PUBLICATIONS

CN 117018504 A—Machine translation, retrieved on Nov. 2025 (Year: 2025).*

Li, J. et al. Gas sensing technology as the key to safety warning of lithium-ion battery: Recent advance. Sensors and Actuators A: Physical 365 (2024): 114890. p. 12; par. 3 and 4 (Year: 2024).*

Giallorenzi, T. et al. Optical-fiber sensors challenge the competition: Resistance to corrosion and immunity to interference head the list of benefits in detecting stimuli ranging from pressure to magnetism. IEEE spectrum 23.9 (1986): 44-50. p. 44; par. 4 (Year: 1989).*

Best, A. et al. Lithium-ion battery safety: A report for the Australian Competition and Consumer Commission (ACCC). 2023, CSIRO, Australia. p. 10; par. 2, p. 12 and Table 3; BMS Features under Fair plus (Year: 2023).*

\* cited by examiner

MONITORING AND EARLY WARNING SYSTEM FOR POWER LITHIUM ION BATTERY TRANSPORT CASE AND MONITORING AND EARLY WARNING METHOD

TECHNICAL FIELD

The present invention relates to the technical field of transportation safety of power lithium ion batteries, and in particular to a monitoring and early warning system for a power lithium ion battery transport case and a monitoring and early warning method.

BACKGROUND ART

A monitoring and early warning system for a power lithium ion battery transport case and a monitoring and early warning method are developed to address potential hazards such as combustion, explosion, and toxic gas release during transportation of the power lithium ion battery (including multiple forms such as cells, modules, and battery packs). Lithium power batteries belong to Class 9 dangerous goods and require transport packaging with high protective performance to control safety risks. However, traditional transport packaging forms such as cartons, wooden cases, and metal cases mainly used currently have obvious limitations in protective performance, lack real-time monitoring and early warning functions, and cannot effectively address the possible thermal runaway risk of the power lithium ion battery.

In CN119471450A, a lithium ion battery thermal runaway early warning system and method based on multi-source parameter monitoring are disclosed. The method includes: acquiring multi-source battery parameters in real time, and marking the multi-source battery parameters as real-time multi-source battery parameters; processing the real-time multi-source battery parameters to extract battery feature parameters; performing fusion analysis on the real-time multi-source battery parameters and extracted battery feature parameters to predict a thermal runaway probability of the lithium ion battery; determining whether to generate an evaluation instruction according to the thermal runaway probability; and evaluating, if the evaluation instruction is generated, a thermal runaway type of the lithium ion battery, and starting active prevention and control measures.

In CN119357838A, an XGBoost-based energy storage battery fire multi-parameter detection method is disclosed. The method includes: step 1, constructing an XGBoost model; step 2, expressing an objective function as a function about the number of samples and the number of trees, and approximating a loss function through second-order expansion of a Taylor formula to optimize the objective function; step 3, iteratively updating, for each sample, a predicted value; and step 4, adjusting, according to actual data of the energy storage battery fire, parameters of the XGBoost model, including a learning rate, a depth of the tree, and a regularization coefficient, and training the model to accurately detect multiple parameters of the energy storage battery fire.

In CN119502701A, a new energy automobile lithium ion battery thermal runaway monitoring system and method are disclosed. The system includes a vehicle-mounted lithium ion battery, a multi-source data acquisition module, a multi-source data fusion module, a hidden Markov model monitoring module, a state identification module, a data analysis processing module, an early warning module, an emergency processing module, a wireless communication module, a cloud platform, and a battery management system. The multi-source data acquisition module is responsible for acquiring multi-dimensional data such as voltage, temperature, and internal resistance of the lithium ion battery. The data fusion module processes the data and then transmits the data to the hidden Markov model monitoring module for state monitoring and prediction.

In CN119097873A, a lithium ion battery thermal runaway early warning and fire extinguishing integrated system is disclosed. The system includes an early warning subsystem, a fire extinguishing subsystem, an oxygen consumption detection subsystem, and a signal analysis processing control subsystem. The early warning subsystem includes a temperature early warning unit, a current voltage-ultrasonic early warning unit, and a gas-acoustic signal early warning unit, which are configured to monitor the temperature, current voltage, ultrasonic signal, gas composition, and acoustic signal of the lithium ion battery in real time. The oxygen consumption detection subsystem includes an oxygen consumption detection analysis unit, which performs thermal runaway heat release statistics, performs data statistics on thermal runaway warning parameters, and finds a thermal runaway heat critical value to prepare for fire extinguishing. The fire extinguishing subsystem includes a fire extinguishing unit, which is configured to quickly activate a fire extinguishing apparatus to extinguish a fire after thermal runaway of the lithium ion battery is confirmed. The signal analysis processing control subsystem includes a signal analysis processing control unit, which is configured to receive and analyze an early warning signal and control the fire extinguishing subsystem to extinguish the fire according to the early warning signal.

In CN119538129A, an intelligent data analysis technology of a lithium ion battery fire hazard detector is disclosed. The occurrence of thermal runaway is predicted by detecting an extremely trace amount of characteristic gas released from the lithium ion battery. Through a large number of experimental tests on different brands of cells, a lithium ion battery thermal runaway first-stage feature model database is established, and an intelligent data analysis algorithm is adopted to analyze detected gas data in real time and compare the gas data with the feature model database, thereby quickly determining whether the lithium ion battery is in an early stage of thermal runaway. This intelligent data analysis algorithm needs to consider various complex conditions and factors, such as environmental temperature, battery aging degree, and charge and discharge states, and is integrated with a battery management system (BMS). Once the hidden danger of thermal runaway of the lithium ion battery is detected, an alarm is immediately sent to the BMS, and corresponding treatment measures are recommended.

However, the above techniques are not accurate enough and are not suitable for use in the environment of the power lithium ion battery transport case.

SUMMARY

In view of the shortcomings of the related art, the present invention aims to provide a novel monitoring and early warning system for a power lithium ion battery transport case and a monitoring and early warning method, in which parameters such as temperature, gas, smoke, and pressure of the battery are monitored to perform thermal runaway early warning during the transportation of the power lithium ion battery, thereby realizing accurate determination of battery thermal runaway early warning.

To solve the foregoing problems, the present invention adopts the following technical solutions.

The present invention provides a monitoring and early warning system for a power lithium ion battery transport case. The system includes a monitoring unit, a data processing unit, a data transmission unit, a power supply unit, a display unit, and a response unit.

The monitoring unit contains temperature sensors, gas sensors, pressure sensors, and smoke sensors.

The monitoring unit is deployed on a lower surface of a case cover, and a sensing apparatus adopts a distributed design and is equipped with the temperature sensors, the gas sensors, the pressure sensors, and the smoke sensors.

The data processing unit is arranged on an inner side of the transport case cover.

The display unit includes a display panel and a display light.

The display unit is arranged on an outer side of the transport case cover; the display panel is able to display battery temperature, gas concentration, smoke concentration, and pressure inside the transport case; the display light emits a photoelectric alarm when determining that thermal runaway of a battery occurs; the power supply unit is a lithium ion battery pack; the power supply unit is arranged on the inner side of the transport case cover to supply power to an entire early warning system; the data transmission unit includes a 4G module and WIFI; the data transmission unit and the data processing unit are integrated in one housing; the response unit includes a release box and alarm information issued by a platform; when the early warning system determines that thermal runaway occurs in the transport case, the release box is opened through an electrical signal, and fire extinguishing material placed in the release box falls to suppress battery flames; the early warning system sends the alarm information to a terminal.

The temperature sensors include non-contact infrared temperature sensors and thermocouples. The infrared temperature sensor is fixed on a fixed small plate. A probe of the thermocouple extends outside a sensor housing. Leads of the infrared temperature sensor and the thermocouple are connected to a collector connection line from a back center of the housing. Several infrared temperature sensors are connected through a CAN bus. Several thermocouples are connected through an ADC line. The sensor housing is screwed to the case cover inside the transport case and vertically irradiates the battery below.

Preferably, the gas sensors include several hydrogen sensors and several carbon monoxide sensors. The sensors are connected through leads and are connected to an RS485 interface on a data collector. The sensor housing is screwed to the case cover inside the transport case.

Preferably, the smoke sensors include several smoke sensors. The sensors are directly connected through leads and are connected to the RS485 interface on the data collector. The sensor housing is screwed to the case cover inside the transport case.

Preferably, the pressure sensors include several pressure sensors. The sensors are connected to each other through a CAN bus and are connected to the data collector. The sensor housing is screwed to the case cover inside the transport case.

Preferably, the data collector includes a main control PCB, a main control chip, data interfaces, and a shell. The main control PCB is fixed at the center of the shell, the main control chip is provided slightly below the middle of the data collector, and the data interfaces are distributed at a left side of the data collector.

Preferably, the data collector includes a communication interface connected to a sensing apparatus. Specifically, the infrared temperature sensor communicates with the data collector in a CAN mode. The thermocouple is connected through an ADC interface of the data collector. The gas sensor adopts an RS485 mode for communication. An RS232 interface is reserved on the data collector to facilitate future function expansion. The data collector further needs to be able to transmit signals from a plurality of sensors of the same type on one data transmission line.

Further, a CAN interface adopts three high-speed communication interfaces, with a baud rate CAN reaching 500 kbps, supporting the simultaneous connection of multiple sensors on a single bus.

Further, the ADC interface adopts one communication interface and a 24-bit high-precision AD sampling chip.

Further, the RS485 interface adopts three communication interfaces, with a baud rate CAN reaching 115,200 kbps, supporting the simultaneous connection of multiple sensors on a single bus.

Further, the interface also needs to reserve one RS232 interface for future system expansion.

Further, the data collector is also provided with three UART interfaces, in which one interface is connected to the 4G module, one interface is connected to WIFI, and one interface is connected to the RS485 interface.

Further, the data collector requires a byte size of 16 MB to store data.

Further, the data collector may store one week of acquired data while uploading continuous signals to a monitoring platform.

Further, a sampling frequency of the data collector is 2 HZ.

Further, a serial port transmission speed of the data collector is not less than 9,600 bps.

Further, the main control PCB in the data collector has a length of 200 mm, a width of 100 mm, and a thickness of 10 mm.

Further, a packaging shell of the data collector has a length of 205.6 mm, a width of 105.6 mm, and a thickness of 11.6 mm.

Preferably, the data transmission unit includes a 4G module, WIFI, and an antenna. Specifically, the 4G module and ZIGBEE are installed inside the collector. The antenna needs to be pulled out to the outside of the transport case for patch installation to ensure the communication signal strength.

Preferably, the display unit includes an LCD display panel, an alarm light, and a control button. Specifically, the display panel is turned on and off through the control button. Further, the display content on the display panel is adjusted and displayed through a touch button. Further, the safety state of the lithium ion battery inside the transport case is displayed through LED flashing.

Further, the display panel displays the battery temperature, $H_2$ concentration, CO concentration, and environmental pressure in the transport case.

Further, the display panel may display first-level or second-level early warning information in the transport case.

The power supply unit includes a power supply battery and a package. A specific battery packaging size is 224 mm×152 mm×73.5 mm.

The response unit includes a release box and alarm information issued by a platform; when the early warning system determines that thermal runaway occurs in the transport case, the release box is opened through an electrical signal, and fire extinguishing material placed in the release box falls to suppress battery flames; the early warning system sends the alarm information to a terminal.

Preferably, the data transmission unit includes a 4G module and WIFI. Specifically, the data collector uploads data to a monitoring platform through the 4G module. When the transport case is transported to a region with unstable signals, the data is reported to a gateway using WIFI and then uploaded to the monitoring platform.

The present invention further provides a monitoring and early warning method based on the foregoing monitoring and early warning system for a power lithium ion battery transport case, including the following specific steps:

S1: placing a lithium ion battery in a transport case, and performing temperature, vibration, impact, and humidity processing on the transport case;

S2: monitoring temperature, gas, smoke, and pressure in the transport case through different types of sensors of a monitoring unit;

S3: obtaining various feature parameters of lithium ion battery risks, and normalizing acquired data;

S4: performing risk classification by monitoring multi-information state data of the lithium ion battery, and calculating feature parameter thresholds of lithium ion battery thermal runaway risks under different transport conditions;

S5: inputting quantified feature values into a clustering algorithm to quantify lithium ion battery thermal runaway risk levels;

S6: establishing, to improve risk identification accuracy and prevent a risk false alarm, a data balancing-ensemble learning algorithm to construct a thermal runaway risk identification model of the power lithium ion battery in the transport case;

S7: setting, through the thermal runaway risk identification model of the power lithium ion battery under the transport conditions, a dynamic threshold and a second-level early warning process, and reporting, if it is identified that there is a thermal runaway risk of the lithium ion battery, an early warning signal to a back-end.

Different transport condition states $X_y(t)$ (temperature Tenv(t) T, vibration V(t), humidity S(t), and impact H(t)) of the battery in the transport case are obtained through the following formula:

$$X_y(t)=[Tenv(t),V(t),S(t),H(t)].$$

Battery thermal runaway risk states $X_d$ (battery temperature $T_{bat}$, H2 concentration $H_2$ in the transport case, CO concentration CO in the transport case, smoke concentration SM in the transport case, and pressure P) and different battery monitoring states $R_y(t)$ under the transport conditions are monitored through the following formulas:

$$X_d(t)=[T_{bat}(t),H_2(t),CO(t),SM(t),P(t)], \text{ and } R_y(t)=[X_y(t),X_d(t)].$$

Lithium ion battery thermal runaway risk feature parameters under different transport conditions are extracted, including a battery temperature rise rate, a H2 concentration change rate, a CO concentration change rate, a smoke concentration change rate, and a pressure change rate, to describe a changing trend of the battery.

$$\Delta T=dT_{bat}/dt, \ \Delta H_2=dH_2/dt, \ \Delta CO=dCO/dt, \ \Delta SM=dSM/dt, \text{ and } \Delta P=dP/dt.$$

A dynamic changing threshold $R^*_i$ is comprehensively determined through the lithium ion battery thermal runaway risk parameters obtained through calculation to further determine a risk degree of the battery. When the feature parameter is lower than $R^*_i$, it indicates that the battery is in a normal state; when the feature parameter is greater than $R^*_i$, it indicates that the battery is in a risky state. $W_T$, $W_{H_2}$, $W_{CO}$, $W_{SM}$, $W_p$ are weights of the battery temperature, the H2 concentration, the CO concentration, the smoke concentration, and the pressure, respectively, and $\Delta T_n$, $\Delta H_{2_n}$, $\Delta CO_n$, $\Delta SM_n$, $\Delta P_n$ are normalized feature values of the battery temperature, the H2 concentration, the CO concentration, the smoke concentration, and the pressure, respectively. Therefore, a comprehensive feature threshold $R^*_i$ is obtained through the following formula:

$$R^*_i=W_T\Delta T_n+W_{H_2}\Delta H_{2_n}+W_{CO}\Delta CO_n+W_{SM}\Delta SM_n+W_p\Delta P_n.$$

Clustering is performed using an algorithm to classify risk probability levels of thermal runaway of the lithium ion battery when different parameters are monitored during transportation; K objects are set through n samples, with each sample having three dimensions, distances d between an object $X_i$ and cluster centroids $C_j$ are compared in sequence, and jth dimension values of $X_i$ and $C_j$ are $X_{it}$, $C_{jt}$:

$$d(X_i, C_j) = \sqrt{\sum_{jt}^{m}(X_{it} - C_{jt})}.$$

$C_L$ is an Lth cluster centroid; $N_L$ is the number of samples in the Lth cluster centroid; a centroid point is recalculated with a mean value of all objects in a current category.

$$C_l = \frac{\sum_{X_i}^{C_L} X_I}{N_l}.$$

The foregoing steps are repeated until the cluster centroid no longer changes, thereby completing clustering. Meanwhile, through an elbow method, the number of categories K of a cluster is determined accordingly.

Through the elbow method, a sum of squared errors (SSE) within the cluster with respect to the number of clusters is evaluated, where x is a data sample point, $C_i$ is an ith cluster where the data sample point x is located, and μ is a centroid of $C_i$.

$$SSE(k) = \sum_{i=1}^{k} \sum_{\mu \in C_i} |x - \mu|^2.$$

The number of samples of battery thermal runaway under transport conditions is small, and the entire data set is unevenly distributed. Therefore, the data set needs to be balanced to make the number of high-risk samples equivalent to the number of low-risk samples.

According to each minority class sample $x_i$, Euclidean distances between $x_i$ and all other minority class samples are calculated to obtain a neighbor interval range of the minority class sample.

Secondly, a sampling rate M is set by evaluating a degree of imbalance among categories in the data set. The sampling rate is adjusted based on a current imbalance ratio. Next, several data samples are randomly selected from a neighborhood of $x_i$ according to the sampling rate M; the number of data samples is determined by M, and a selected neighboring data sample is recorded as $\bar{x}$.

7

Finally, a new minority class sample is generated using the selected $\bar{x}$, where $\lambda$ is a random number between 0 and 1, and a newly generated data sample is $x_n$.

$$x_n = x_i + (\bar{x} - x_i).$$

A learning algorithm is adopted; guess values of all samples are first initialized, and after a loss function is determined, predicted values of occurrence probabilities of thermal runaway and derivatives of the loss function are obtained; then, based on the foregoing values, a new decision tree is created, and predicted results of the new decision tree are added to the previous guess values; and finally, derivatives of the loss function are obtained again based on a second step.

(1) An objective function combines a loss function S and a regularization term $\Omega$: the loss function measures a difference between the predicted value and an actual value, and the regularization term penalizes complexity of the model to prevent overfitting. $y_i$ is the actual value, $\hat{y}_i$ is a predicted value of an ith instance, $f_k$ is a kth tree, and K is a total number of trees; the objective function for a given step is defined as:

$$Obj = \sum_{i=1}^{n} S(y_i - \hat{y}_i) + \sum_{k=1}^{K} \Omega(f_k).$$

(2) Gradient information: based on gradient boosting, an improvement is made to approximate curvature of the loss function accurately using first-order gradient information and second-order gradient information. For a given loss function S, gradients gi and hi of each instance are calculated as follows:

$$g_i = \partial_{\hat{y}_i} S(y_i, \hat{y}_i), \text{ and } h_i = \partial_{\hat{y}_i}^2 S(y_i, \hat{y}_i).$$

(3) Decision tree construction: for each decision tree, an optimal split point is found by enumerating all possible split points of all features; this process is based on calculation of structure scores, and the structure scores adopt gradient statistics of data points that fall into each split region, where L and R represent a left sub-region and a right sub-regions after splitting, respectively; T represents an entire region before splitting; $\lambda$ and $\gamma$ are regularization parameters; a gain obtained through splitting is given by the following formula:

$$Gain = \frac{1}{2}\left[\frac{\left(\sum_i^L g_i\right)^2}{\sum_i^L h_i + \lambda} + \frac{\left(\sum_i^R g_i\right)^2}{\sum_i^R h_i + \lambda} - \frac{\left(\sum_i^T g_i\right)^2}{\sum_i^T h_i + \lambda}\right] - \gamma.$$

For an imbalanced data-multi-classification identification model, the accuracy, precision, recall, F-score, and AUC value usually need to be used as evaluation metrics to perform macro average calculation and micro average calculation. Calculation is performed based on confusion matrix calculation metrics.

TABLE 1

| | Confusion matrix calculation metric | | |
| --- | --- | --- | --- |
| | Identification-low risk | Identification-medium risk | Identification-high risk |
| True-low risk | $a_1$ | $a_2$ | $a_3$ |
| True-medium risk | $b_1$ | $b_2$ | $b_3$ |
| True-high risk | $c_1$ | $c_2$ | $c_3$ |

8

(1) Accuracy: it represents the proportion of the number of correctly identified risk levels to the total number of samples (i.e., a sum of all elements of the confusion matrix). Calculation is performed using the low-risk category as an example, with other categories following the same method.

$$accuracy = \frac{a_1 + b_2 + c_3}{a_1 + a_2 + \ldots + c_2 + c_3}.$$

(2) Precision: it represents the proportion of the number of thermal runaway risk levels actually caused by a transport condition to the number of thermal runaway risk levels identified as being caused by this transport condition. Calculation is performed using the low-risk category as an example, with other categories following the same method.

$$precision = \frac{a_1}{a_1 + b_1 + c_1}.$$

(3) Recall, also referred to as sensitivity: it represents the proportion of the number of actual risk levels to the number of identified risk levels. Calculation is performed using the low-risk category as an example, with other categories following the same method.

$$recall = \frac{a_1}{a_1 + a_2 + a_3}.$$

(4) Comprehensive evaluation metric (F-score): a weighted harmonic mean of accuracy and precision is calculated.

In particular, when a parameter is used, it becomes the most commonly used F1-score:

$$F - score = \frac{(a^2 + 1) \cdot precison \cdot recall}{a^2 \cdot (precison + recall)}.$$

(5) Macro average involves calculating the evaluation metrics independently for each category and then averaging them so that macro average values of precision, recall, and F1-score may be calculated.

$$Macro-F1 = \frac{2 \times Macro\_p \times Macro\_r}{Macro\_p + Macro\_r}.$$

Based on the thermal runaway risk identification model of the power lithium ion battery under transport conditions, the thermal runaway monitoring and early warning method for the lithium ion battery under different transport conditions is obtained, including a dynamic early warning threshold and an early warning process.

Beneficial effects are as follows: (1) According to this system, based on intelligent monitoring and early warning technology, multiple sensors (temperature, gas, pressure, smoke sensors, and the like) are provided in the power lithium ion battery transport case to acquire transportation environment and battery state data, and the data is uploaded to the monitoring platform through wireless communication technology. When an abnormal condition is detected, the system can send the early warning signal in time. The early warning system can not only can send the early warning signal, but also activate the response unit to release the fire extinguishing material. In addition, emergency response measures are performed. Through the fusion processing of multi-sensor data and various transport condition parameters, the probability of thermal runaway of the lithium ion battery can be accurately evaluated, the false alarm rate can be reduced, and the timeliness of early warning can be improved.

(2) The model combines multiple transport conditions (temperature, vibration, impact, and humidity) and multi-dimensional sensing parameters (temperature, gas, smoke, and pressure), classifies the risk levels through the clustering algorithm and the ensemble learning algorithm, quantifies the thermal runaway degree using feature normalization and weighted comprehensive metrics, introduces data balancing to alleviate the small sample bias, constructs an ensemble learning model to classify and identify thermal runaway, thereby improving the thermal runaway early warning accuracy. Through this system, the transport state of the power lithium ion battery may be clearly and comprehensively monitored, thereby achieving efficient and accurate early warning and risk prevention and control, providing valuable time for emergency rescue, minimizing accident losses and risks, and ensuring safe and stable transportation. The development and application of this method and system are of great significance to ensure the transportation safety of the power lithium ion battery.

(3) Due to different transportation environments and different types of transported batteries, the early warning method is provided based on the identification model of the power lithium ion battery in the transport case. In addition, the changing trends of the features are used, rather than simply setting a threshold statically.

(4) In addition, the emergency response unit is provided, which enables a faster response to fires of the lithium ion battery in the transport case, thereby ensuring the safety of personnel and property.

DETAILED DESCRIPTION

Figure 1:
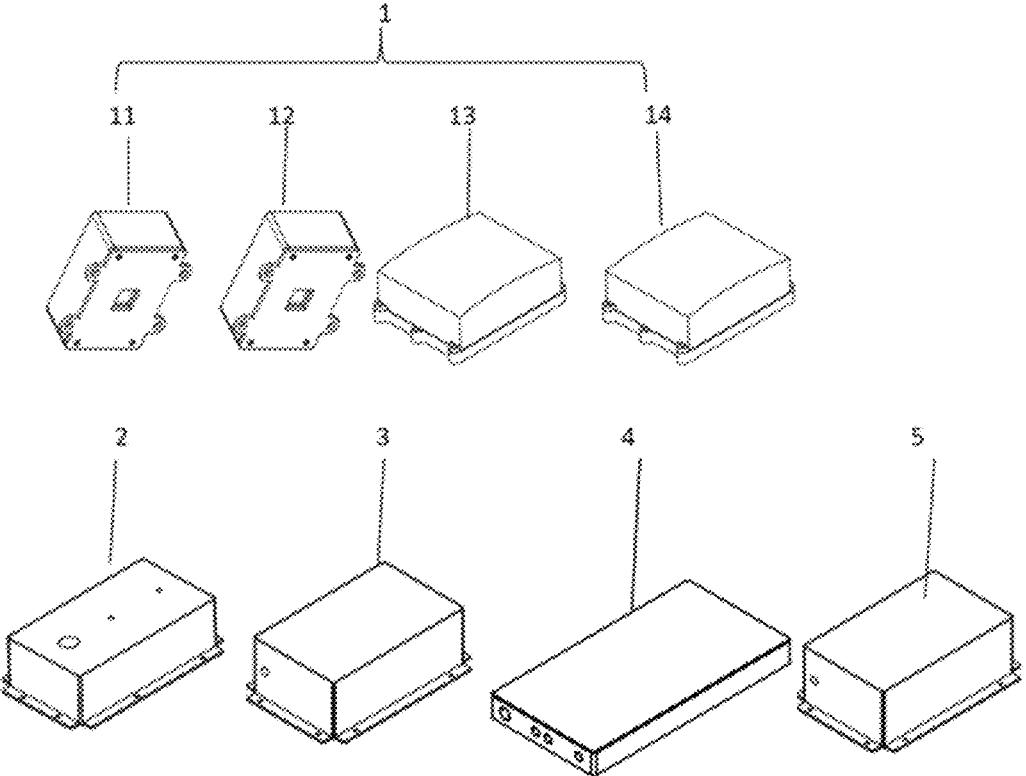
FIG. 1 is a diagram of a monitoring and early warning apparatus for a power lithium ion battery transport case according to the present invention.
Figure 2:
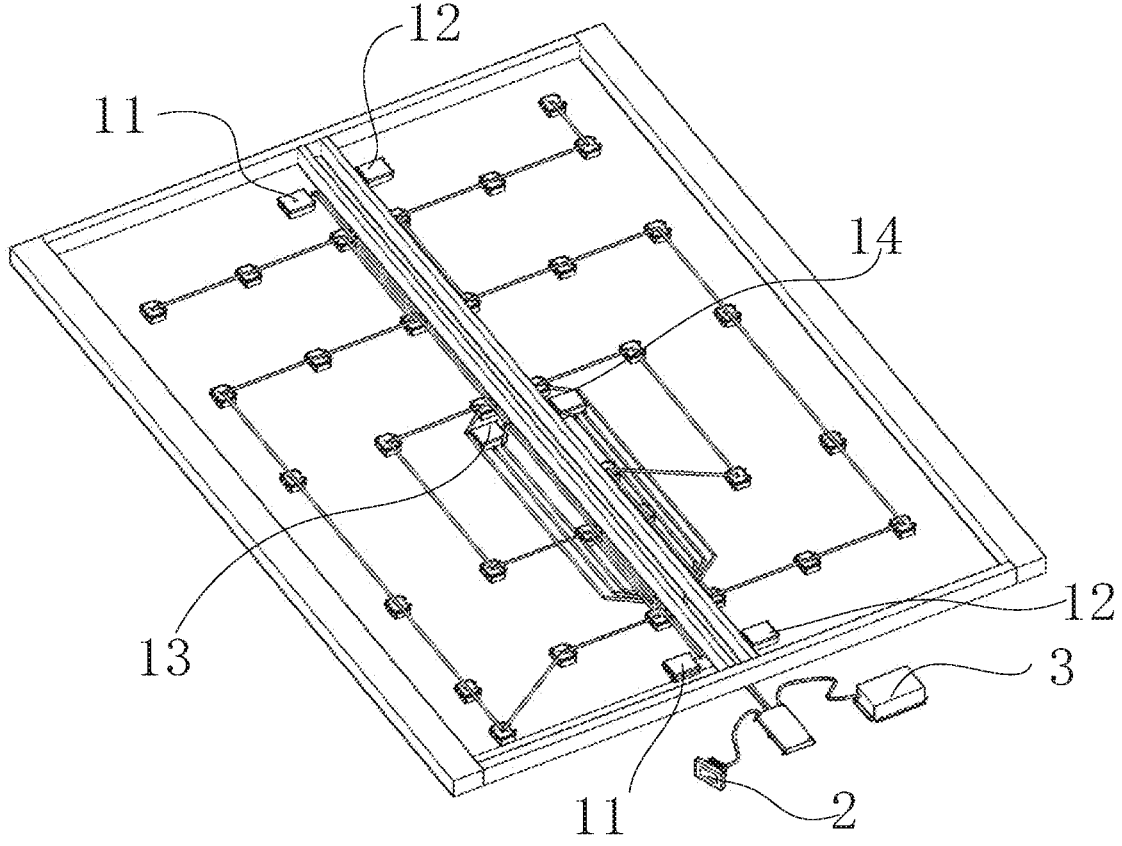
FIG. 2 is a layout diagram of an early warning system on a transport case cover.
Figure 3:
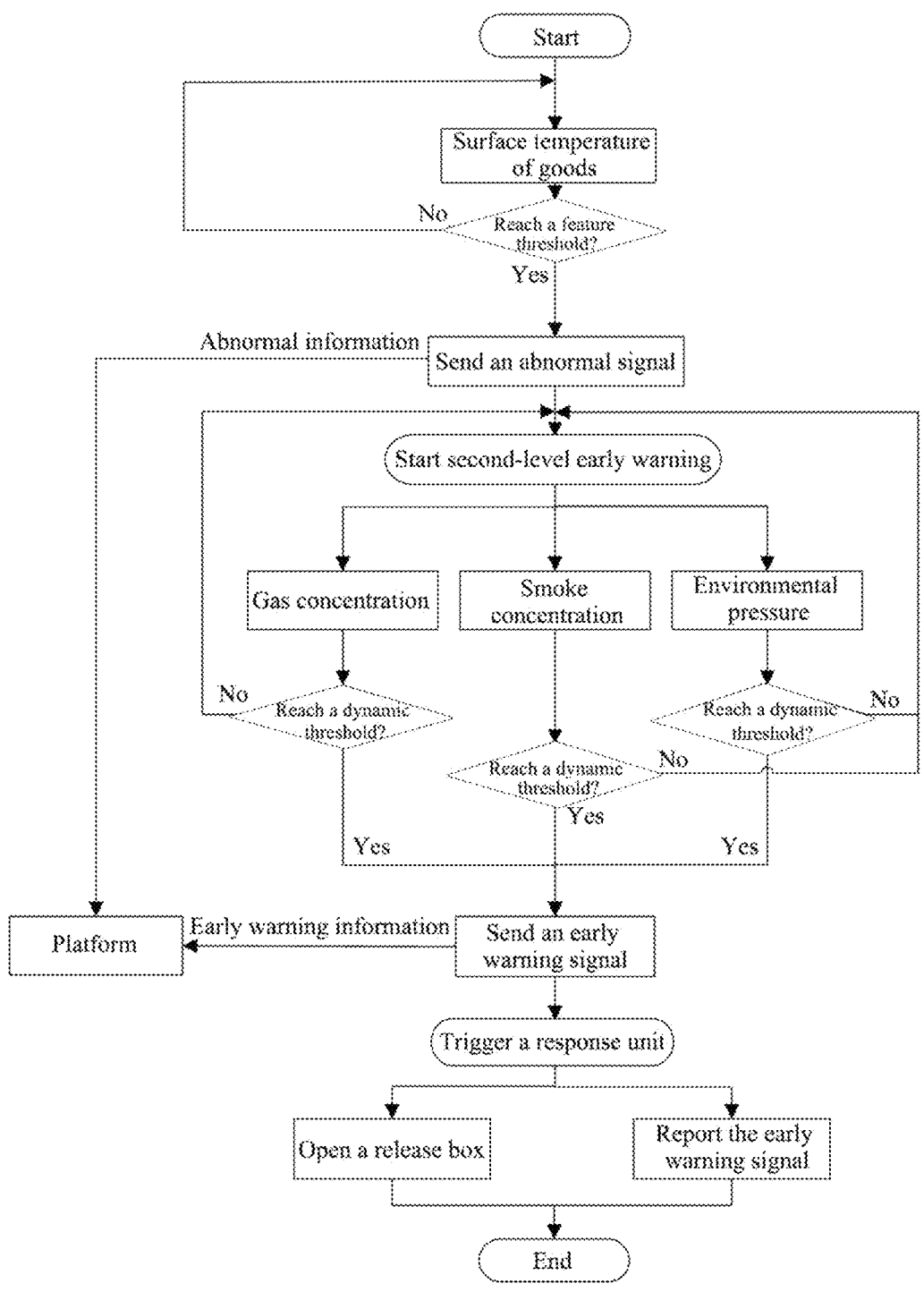
FIG. 3 is an early warning flowchart.

For ease of understanding by a person skilled in that art, the present invention is further described below in conjunction with the embodiments, and the contents mentioned in the implementations are not intended to limit the present invention.

A monitoring and early warning system for a power lithium ion battery transport case includes a sensing apparatus 1 and a data acquisition and transmission unit 4. A display unit 2 is connected to the data acquisition and transmission unit 4 through a lead, the data acquisition and transmission unit 4 sends an electrical signal to a response unit 5, and a power supply unit 3 supplies power to the entire system. The sensing apparatus 1 includes H2 sensors 11, CO sensors 12, infrared temperature sensors 13 and pressure sensors 14.

A monitoring and early warning method based on the foregoing monitoring and early warning system for a power lithium ion battery transport case is provided, including the following specific steps.

The lithium ion battery is placed in a transport case, temperature, vibration, impact, and humidity processing is performed on the transport case, and each transport condition is classified into three dimensions, i.e., low, normal, and high, to obtain different transport condition states $X_y(t)$ (temperature Tenv(t) T, vibration V(t), humidity S(t), and impact H(t)) of the battery in the transport case.

$$X_y(t)=[Tenv(t),V(t),S(t),H(t)].$$

Battery thermal runaway risk states $X_d$ (battery temperature $T_{bat}$, H2 concentration $H_2$ in the transport case, CO concentration CO in the transport case, smoke concentration SM in the transport case, and pressure P) and different battery monitoring states $R_y(t)$ under the transport conditions are monitored through the following formulas:

$X_d(t)=[T_{bat}(t),H_2(t),CO(t),SM(t),P(t)]$. The temperature, gas, smoke, and pressure in the transport case are monitored through different types of sensors of a monitoring unit, and the data is shown in the following table.

TABLE 2

| Monitoring data of monitoring and early warning system | | | | |
|---|---|---|---|---|
| Transport case Serial number | Time (s) | Sensor Serial number | Sensor type | Value |
| 1 | 00:00:14 | 1 | Temperature | 13 |
| 1 | 00:00:14 | 2 | Temperature | 13 |
| 1 | 00:00:14 | 01 | CO | 0 |
| 1 | 00:00:14 | 02 | CO | 0 |
| 1 | 00:00:15 | 010 | Smoke | 0 |
| 1 | 00:00:15 | 011 | Smoke | 0 |
| 1 | 00:00:15 | 0111 | Pressure | 0 |
| . . . | . . . | . . . | . . . | . . . |

Various feature parameters of lithium ion battery risks are obtained, and acquired data is normalized through score calculation.

Risk classification is performed by monitoring multi-information state data of the lithium ion battery, including the battery temperature and a temperature rise rate, the H2 concentration and a change rate, the CO concentration and a change rate, the smoke concentration and a change rate, and a pressure value and a change rate. The feature parameter thresholds of lithium ion battery thermal runaway risks under different transport conditions are calculated.

TABLE 3

| Feature parameter threshold of thermal runaway | | | | | |
|---|---|---|---|---|---|
| Monitoring parameter | Battery temperature | CO | $H_2$ | Smoke | Pressure |
| Threshold | 100° C. | 10 ppm | 10 ppm | 10 ppm | 0.25 kpa |

Thermal runaway risk scores of 5 feature metrics under 4 different transport conditions are calculated through the interquartile range method and normalization, and thermal runaway levels of the lithium ion battery are quantified accord to the scores.

TABLE 4

| | Thermal runaway risk score | | | | |
|---|---|---|---|---|---|
| Serial number | Temperature | $H_2$ | CO | Smoke | Pressure |
| 1 | 0.006 | 0.164 | 0.164 | 0.000 | 0.000 |
| 2 | 0.187 | 0.210 | 0.210 | 0.000 | 0.000 |
| 3 | 0.075 | 0.000 | 0.000 | 0.000 | 0.000 |
| 4 | 0.049 | 0.142 | 0.142 | 0.000 | 0.001 |
| 5 | 0.247 | 0.249 | 0.249 | 0.000 | 0.000 |
| . . . | . . . | . . . | . . . | . . . | . . . |

A dynamic changing threshold $R^*_i$ is comprehensively determined through the lithium ion battery thermal runaway risk parameters obtained through calculation to further determine a risk degree of the battery. When the feature parameter is lower than $R^*_i$, it indicates that the battery is in a normal state; when the feature parameter is greater than $R^*_i$, it indicates that the battery is in a risky state.

First, weights of the battery temperature, the H2 concentration, the CO concentration, the smoke concentration, and the pressure are calculated.

$$W_T = 0.287, W_{H_2} = 0.196, W_{CO} = 0.196, W_{SM} = 0.182, W_P = 0.139.$$

$\Delta T_n$, $\Delta H_{2_n}$, $\Delta CO_n$, $\Delta SM_n$, $\Delta P_n$ are normalized feature values of the battery temperature, the H2 concentration, the CO concentration, the smoke concentration, and the pressure, respectively. Therefore, a comprehensive feature threshold $R^*_i$ is obtained through the following formula:

$$R^*_i = W_T \Delta T_n + W_{H_2} \Delta H_{2_n} + W_{CO} \Delta CO_n + W_{SM} \Delta SM_n + W_P \Delta P_n = 0.056.$$

Clustering is performed using an algorithm to classify risk probability levels of thermal runaway of the lithium ion battery when different parameters are monitored during transportation; K objects are set through n samples, with each sample having three dimensions, distances d between an object $X_i$ and cluster centroids $C_j$ are compared in sequence, and jth dimension values of $X_i$ and $C_j$ are $X_{it}$, $C_{jt}$:

$$d(X_i, C_j) = \sqrt{\sum_t^m (X_{it} - C_{jt})}.$$

$C_L$ is an Lth cluster centroid; $N_L$ is the number of samples in the Lth cluster centroid; a centroid point is recalculated with a mean value of all objects in a current category.

$$C_l = \frac{\sum_{X_i}^{C_L} X_I}{N_l}.$$

The foregoing steps are repeated until the cluster centroid no longer changes, thereby completing clustering. Meanwhile, through an elbow method, the number of categories K of a cluster is determined accordingly.

Through the elbow method, an SSE within the cluster with respect to the number of clusters is evaluated, where x is a data sample point, $C_i$ is an ith cluster where the data sample point x is located, and $\mu$ is a centroid of $C_i$.

$$SSE(k) = \sum_{i=1}^k \sum_{\mu \in C_i} |x - \mu|^2.$$

Clustering results are shown in the following table. It can be seen from the results in the table that for a category 1, the proportion is the lowest, and for a category 3, the proportion is the highest. Therefore, a normal state, a thermal runaway low risk, and a thermal runaway high risk are classified.

TABLE 5

| | K-means clustering result | | |
|---|---|---|---|
| Cluster category | Number of samples | Proportion/% | Final cluster centroid |
| 1 | 24 | 4.7% | 0.33 |
| 2 | 179 | 34.9% | 0.16 |
| 3 | 309 | 60.4% | 0.06 |

The number of samples of battery thermal runaway under transport conditions is small, and the entire data set is unevenly distributed. Therefore, the data set needs to be balanced to make the number of high-risk samples equivalent to the number of low-risk samples.

According to each minority class sample $x_i$, Euclidean distances between $x_i$ and all other minority class samples are calculated to obtain a neighbor interval range of the minority class sample.

Secondly, a sampling rate M is set by evaluating a degree of imbalance among categories in the data set. The sampling rate is adjusted based on a current imbalance ratio. Next, several data samples are randomly selected from a neighborhood of $x_i$ according to the sampling rate M; the number of data samples is determined by M, and a selected neighboring data sample is recorded as $\bar{x}$.

Finally, a new minority class sample is generated using the selected $\bar{x}$, where $\lambda$ is a random number between 0 and 1, and a newly generated data sample is $x_n$.

$$x_n = x_i + (\bar{x} - x_i).$$

A learning algorithm is adopted; guess values of all samples are first initialized, and after a loss function is determined, predicted values of occurrence probabilities of thermal runaway and derivatives of the loss function are obtained; then, based on the foregoing values, a new decision tree is created, and predicted results of the new decision tree are added to the previous guess values; and finally, derivatives of the loss function are obtained again based on a second step.

(1) An objective function combines a loss function S and a regularization term $\Omega$: the loss function measures a difference between the predicted value and an actual value, and the regularization term penalizes complexity of the model to prevent overfitting. $y_i$ is the actual value, $\hat{y}_i$ is a predicted value of an ith instance, $f_k$ is a kth tree, and K is a total number of trees; the objective function for a given step is defined as:

$$Obj = \sum_{i=1}^n S(y_i - \hat{y}_i) + \sum_{k=1}^K \Omega(f_k).$$

(2) Gradient information: based on gradient boosting, an improvement is made to approximate curvature of the loss function accurately using first-order gradient information and second-order gradient information. For a given loss function S, gradients gi and hi of each instance are calculated as follows:

$$g_i = \partial_{\hat{y}_i} S(y_i, \hat{y}_i), \text{ and } h_i = \partial_{\hat{y}_i}^2 S(y_i, \hat{y}_i).$$

(3) Decision tree construction: for each decision tree, an optimal split point is found by enumerating all possible split points of all features; this process is based on calculation of structure scores, and the structure scores adopt gradient statistics of data points that fall into each split region, where L and R represent a left sub-region and a right sub-regions after splitting, respectively; T represents an entire region before splitting; λ and γ are regularization parameters; a gain obtained through splitting is given by the following formula:

$$\text{Gain} = \frac{1}{2}\left[\frac{\left(\sum_i^L g_i\right)^2}{\sum_i^L h_i + \lambda} + \frac{\left(\sum_i^R g_i\right)^2}{\sum_i^R h_i + \lambda} - \frac{\left(\sum_i^T g_i\right)^2}{\sum_i^T h_i + \lambda}\right] - \gamma.$$

For an imbalanced data-multi-classification identification model, the accuracy, precision, recall, F-score, and AUC value usually need to be used as evaluation metrics to perform macro average calculation and micro average calculation. Calculation is performed based on confusion matrix calculation metrics.

(1) Accuracy: it represents the proportion of the number of correctly identified risk levels to the total number of samples (i.e., a sum of all elements of the confusion matrix). Calculation is performed using the low-risk category as an example, with other categories following the same method.

$$\text{accuracy} = \frac{a_1 + b_2 + c_3}{a_1 + a_2 + \ldots + c_2 + c_3}.$$

(2) Precision: it represents the proportion of the number of thermal runaway risk levels actually caused by a transport condition to the number of thermal runaway risk levels identified as being caused by this transport condition. Calculation is performed using the low-risk category as an example, with other categories following the same method.

$$\text{precision} = \frac{a_1}{a_1 + b_1 + c_1}.$$

(3) Recall, also referred to as sensitivity: it represents the proportion of the number of actual risk levels to the number of identified risk levels. Calculation is performed using the low-risk category as an example, with other categories following the same method.

$$\text{recall} = \frac{a_1}{a_1 + a_2 + a_3}.$$

(4) Comprehensive evaluation metric (F-score): a weighted harmonic mean of accuracy and precision is calculated.

In particular, when a parameter is used, it becomes the most commonly used F1-score:

$$F - \text{score} = \frac{(a^2 + 1) \cdot \text{precison} \cdot \text{recall}}{a^2(\text{precison} + \text{recall})}.$$

(5) Macro average involves calculating the evaluation metrics independently for each category and then averaging them so that macro average values of precision, recall, and F1-score may be calculated.

$$\text{Macro} - F1 = \frac{2 \times \text{Macro\_p} \times \text{Macro\_r}}{\text{Macro\_p} + \text{Macro\_r}}.$$

These risk samples are labeled as three categories, i.e., 0, 1, and 2. Then, data modeling is performed in the Spyder environment using the Python programming language. First, a vehicle trajectory data set is imported by invoking numpy and pandas libraries, and feature metrics of all samples and the corresponding risk labels are read. Secondly, three algorithms, i.e., XGBoost, LGBM, and LCE, are introduced into a Sklearn machine learning library to directly construct a model. Common data set division ratios include 70% for a training set and 30% for a testing set, 80% for the training set and 20% for the testing set, or the like. A risky driving behavior identification model is established, and the performance of the model is evaluated. Model performance evaluation metrics are shown in Table 6.

TABLE 6

| Performance evaluation of ensemble learning algorithm (Macro) | | | | |
|---|---|---|---|---|
| Model category | Precision (%) | Recall (%) | F1-score | AUC |
| XGBoost | 46.06 | 47.66 | 0.465 | 0.835 |

Based on the thermal runaway risk identification model of the power lithium ion battery under transport conditions, the thermal runaway monitoring and early warning method for the lithium ion battery under different transport conditions is obtained, including a dynamic early warning threshold and two early warning processes.

The specific steps are as follows.

At S1, according to the volume of the transport case, several monitoring sections are arranged, including environmental parameters such as H2 concentration, CO concentration, monitoring point temperature, and pressure in the transport equipment. Sensors are arranged in the transport equipment to acquire data, and an early warning threshold is set.

At S2, the non-contact temperature sensor is started to monitor the battery surface temperature and acquire the H2 concentration, CO concentration, monitoring point temperature, and environmental pressure data in real time. The real-time acquired data is compared and analyzed to determine whether a thermal runaway determination condition is met.

At S3, when the battery temperature reaches the set threshold, it is determined that the thermal runaway low risk occurs, and the first-level early warning is triggered. In this case, a temperature value monitored by the non-contact temperature sensor rises abnormally, and the system will automatically turn on the H2 sensor, the CO sensor, the smoke sensor, and the pressure sensor and upload abnormal information to the remote monitoring platform.

At S4, After the first-level early warning, a second-level early warning mechanism is started. The H2 sensor and the CO sensor are adopted to monitor the gas concentration during thermal runaway, the pressure sensor is adopted to monitor the environmental pressure in transport case, and the non-contact temperature sensor is adopted to monitor the monitoring point temperature. When any metric in the monitoring data exceeds the set threshold, the system will immediately send early warning information to the remote monitoring platform and start a corresponding response process.

At S5, when the second-level early warning is triggered, that is, the thermal runaway high risk occurs, the system automatically selects an emergency plan and issues a disposal instruction to the driver through vehicle-mounted and ship-mounted terminals (applicable to road, railway, and waterway transportation). For air transportation, the early warning information is transmitted to the cockpit through aircraft's cargo hold Wi-Fi and responded to according to a predetermined emergency processing process.

At S6, meanwhile, the system activates the top cover release box to start the fire extinguishing process through the internal fire extinguishing material automatic fire extinguisher to minimize accident losses caused by thermal runaway.

It will be understood by a person skilled in the art that, unless otherwise defined, all terms (including technical and scientific terms) used herein have the same meaning as commonly understood by a person skilled in the art to which the present invention belongs. It will be further understood that terms such as those defined in general dictionaries are to be understood as having a meaning consistent with the meaning in the context of the related art and are not to be interpreted in an idealized or overly formal sense unless specifically defined as herein.

It should be understood that the above detailed description of the technical solutions of the present invention using preferred embodiments is illustrative rather than restrictive. Based on reading the specification of the present invention, a person skilled in the art may modify the technical solutions recorded in the embodiments or make equivalent replacements to some of the technical features thereof. However, these modifications or replacements do not make the essence of the corresponding technical solutions detached from the spirit and scope of the technical solutions of the embodiments of the present invention.

What is claimed is:

1. A multi-information monitoring-based transported battery thermal runaway early warning method based on a monitoring and early warning system installed in a transport case: comprising the following steps:

S1: placing a lithium ion battery in the transport case, and performing temperature, vibration, impact, and humidity processing on the transport case;

S2: monitoring temperature, gas, smoke, and pressure in the transport case through sensors of a monitoring unit;

S3: obtaining various feature parameters of lithium ion battery risks, and normalizing acquired data;

S4: performing risk classification by monitoring multi-information state data of the lithium ion battery, and calculating feature parameter thresholds of lithium ion battery thermal runaway risks under different transport conditions;

S5: inputting quantified feature values into a clustering algorithm to quantify lithium ion battery thermal runaway risk levels;

S6: establishing, to improve risk identification accuracy and prevent a risk false alarm, a data balancing-ensemble learning algorithm to construct a thermal runaway risk identification model of the power lithium ion battery in the transport case; and S7 setting, through the thermal runaway risk identification model of the power lithium ion battery under the transport conditions, a dynamic threshold and a second-level early warning process, and reporting, if it is identified that there is a thermal runaway risk of the lithium ion battery, an early warning signal to a back-end;

wherein the monitoring and early warning system comprises the monitoring unit, a data processing unit, a data transmission unit, a power supply unit, a display unit, and a response unit;

sensors of the monitoring unit comprise temperature sensors, gas sensors, pressure sensors, and smoke sensors;

the monitoring unit is deployed on a lower surface of a case cover, and a sensing apparatus adopts a distributed design and is equipped with the temperature sensors, the gas ($H2$, $CO$ sensors, the smoke sensors, and the pressure sensors;

the data processing unit is arranged on an inner side of the case cover;

the display unit comprises a display panel and a display light;

the display unit is arranged on an outer side of the case cover; the display panel is able to display battery temperature, gas concentration, smoke concentration, and pressure inside the transport case; the display light emits a photoelectric alarm when determining that thermal runaway of the lithium ion battery occurs;

the power supply unit is a lithium ion battery pack;

the power supply unit is arranged on the inner side of the case cover to supply power to the monitoring and early warning system;

the data transmission unit comprises a 4G module and WIFI;

the data transmission unit and the data processing unit are integrated in one housing;

the response unit comprises a release box and alarm information issued by a platform; when the monitoring and early warning system determines that thermal runaway occurs in the transport case, the release box is opened through an electrical signal, and fire extinguishing material placed in the release box falls to suppress battery flames; the monitoring and early warning system sends the alarm information to a terminal.

2. The method according to claim 1, wherein different transport condition states $X_y(t)$ (temperature $Tenv(t)$ $T$, vibration $V(t)$, humidity $S(t)$, and impact $H(t)$) of the lithium ion battery in the transport case in S1 are obtained through the following formula:

$$X_y(t)=[Tenv(t),V(t),S(t),H(t))].$$

3. The method according to claim 2, wherein, in S2, battery thermal runaway risk states $X_d$ (battery temperature $T_{bat}$, $H2$ concentration $H_2$ in the transport case, $CO$ concentration $CO$ in the transport case, smoke concentration $SM$ in the transport case, and pressure $P$) and different battery monitoring states $R_y(t)$ under the transport conditions are obtained through the following formulas:

$$X_d(t)=[T_{bat}(t),H_2(t),CO(t),SM(t),P(t)], \text{ and } R_y(t)=[X_y(t),X_d(t))]$$

lithium ion battery thermal runaway risk feature parameters under different transport conditions are extracted, comprising the lithium ion battery temperature and a temperature rise rate, the $H2$ concentration and a change rate, the $CO$ concentration and a change rate, the smoke concentration and a change rate, and a pressure value and a change rate, to describe a changing trend of the lithium ion battery, $$\Delta T=dT_{bat}/dt; \ \Delta H_2=dH_2/dt; \ \Delta CO=dCO/dt; \ \Delta SM=dSM/dt; \text{ and } \Delta P=dP/dt;$$

a dynamic changing threshold $R^*_i$ is comprehensively determined through the lithium ion battery thermal runaway risk parameters to further determine a risk degree of the lithium ion battery; when the feature parameter is lower than $R^*_i$, it indicates that the lithium ion battery is in a normal state; when the feature parameter is greater than $R^*_i$, it indicates that the lithium ion battery is in a risky state; a comprehensive feature threshold $R^*_i$ is obtained through the following formula:

$$R^*_i = W_T \Delta T_n + W_{H_2} \Delta H_{2_n} + W_{CO} \Delta CO_n + W_{SM} \Delta SM_n + W_P \Delta P_n,$$

wherein $W_T$, $W_{H_2}$, $W_{CO}$, $W_{SM}$, $W_p$ are weights of the battery temperature, the H2 concentration, the CO concentration, the smoke concentration, and the pressure, respectively, and $\Delta T_n$, $\Delta H_{2_n}$, $\Delta CO_n$, $\Delta SM_n$, $\Delta P_n$ are normalized feature values of the battery temperature, the H2 concentration, the CO concentration, the smoke concentration, and the pressure, respectively.

4. The method according to claim 1, wherein in S5, clustering is performed using an algorithm to classify risk probability levels of thermal runaway of the lithium ion battery when different parameters are monitored during transportation; K objects are set through n samples, with each sample having three dimensions, distances d between an object $X_i$ and cluster centroids $C_j$ are compared in sequence, and jth dimension values of $X_i$ and $C_j$ are $X_{it}$, $C_{jt}$:

$$d(X_i, C_j) = \sqrt{\sum_t^m (X_{it} - C_{jt})},$$

wherein $C_L$ is an Lth cluster centroid; $N_L$ is the number of samples in the Lth cluster centroid; a centroid point is recalculated with a mean value of all objects in a current category;

$$C_l = \frac{\sum_{X_i}^{C_L} X_l}{N_l};$$

the foregoing steps are repeated until the cluster centroid no longer changes, thereby completing clustering; meanwhile, the number of K of a cluster is determined accordingly;

a change of a sum of squared errors (SSE) within the cluster with respect to the number of clusters is determined, $$SSE(k) = \sum_{i=1}^k \sum_{\mu \in C_i} |x - \mu|^2,$$

wherein SSE(k) is the SSE within the cluster, x is a data sample point, $C_i$ is an ith cluster where the data sample point x is located, and $\mu$ is a centroid of $C_i$.

5. The method according to claim 1, wherein a data set is balanced to make the number of high-risk samples equivalent to the number of low-risk samples;

according to each minority class sample $x_i$, Euclidean distances between $x_i$ and all other minority class samples are calculated to obtain a neighbor interval range of the minority class sample;

a sampling rate M is set by evaluating a degree of imbalance among categories in the data set, and several data samples are randomly selected from a neighborhood of $x_i$ according to the sampling rate M; the number of data samples is determined by M, and a selected neighboring data sample is recorded as $\bar{x}$;

a new minority class sample is generated using the selected $\bar{x}$, wherein $\lambda$ is a random number between 0 and 1, and a newly generated data sample is $x_n$;

$$x_n = x_i + (\bar{x} - x_i);$$

and in S6, a learning algorithm is adopted; guess values of all samples are first initialized, and after a loss function is determined, predicted values of occurrence probabilities of thermal runaway and derivatives of the loss function are obtained; then, based on the foregoing values, a new decision tree is created, and predicted results of the new decision tree are added to the previous guess values; and finally, derivatives of the loss function are obtained again based on a second step;

(1) an objective function combines a loss function S and a regularization term $\Omega$: the loss function measures a difference between the predicted value and an actual value, and the regularization term penalizes complexity of the model to prevent overfitting; $y_i$ is the actual value, $\hat{y}_i$ is a predicted value of an ith instance, $f_k$ is a kth tree, and K is a total number of trees;

the objective function for a given step is defined as:

$$Obj = \sum_{i=1}^n S(y_i - \hat{y}_i) + \sum_{k=1}^K \Omega(f_k);$$

(2) gradient information: based on gradient boosting, an improvement is made to approximate curvature of the loss function accurately using first-order gradient information and second-order gradient information;

(3) decision tree construction: for each decision tree, an optimal split point is found by enumerating all possible split points of all features; this process is based on calculation of structure scores, and the structure scores adopt gradient statistics of data points that fall into each split region, wherein L and R represent a left sub-region and a right sub-regions after splitting, respectively; T represents an entire region before splitting; $\lambda$ and $\gamma$ are regularization parameters; a gain obtained through splitting is given by the following formula:

$$Gain = \frac{1}{2}\left[ \frac{\left(\sum_i^L g_i\right)^2}{\sum_i^L h_i + \lambda} + \frac{\left(\sum_i^R g_i\right)^2}{\sum_i^R h_i + \lambda} - \frac{\left(\sum_i^T g_i\right)^2}{\sum_i^T h_i + \lambda} \right] - \gamma.$$

6. The method according to claim 1, wherein batter data is acquired by arranging the temperature sensors, the gas sensors, the pressure sensors, and the smoke sensors inside the transport case; the temperature sensors, the gas sensors, the smoke sensors, and the pressure sensors are non-contact sensors and are packaged inside respective housings.

7. The method according to claim 1, wherein the response unit is provided with a fire extinguishing release box installed under the case cover; when the data processing unit determines that thermal runaway of the lithium ion battery in the transport case occurs, the electrical signal is sent to open the release box, and the fire extinguishing material inside the release box falls to suppress flames emitted from the lithium ion battery.

8. The method according to claim 1, wherein the display panel is able to display the battery temperature, the gas concentration, the smoke concentration, and the pressure inside the transport case;

the display light is an LED alarm light; when the data processing unit determines that thermal runaway of the lithium ion battery in the transport case occurs, the LED alarm light displays red and emits the photoelectric alarm.

* * * * *